United States Patent

Cregger et al.

(10) Patent No.: US 7,960,169 B2
(45) Date of Patent: Jun. 14, 2011

(54) BIOLOGICAL INDICATOR

(75) Inventors: Tricia A. Cregger, Fairlawn, OH (US); Phillip P. Franciskovich, Concord, OH (US); Mark J. Duda, Twinsburg, OH (US); Robert E. Bellow, Jr., Madison, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 12/658,350

(22) Filed: Feb. 5, 2010

(65) Prior Publication Data

US 2010/0143930 A1    Jun. 10, 2010

Related U.S. Application Data

(63) Continuation of application No. 12/082,642, filed on Apr. 11, 2008, now Pat. No. 7,741,107, which is a continuation of application No. 11/135,719, filed on May 24, 2005, now Pat. No. 7,416,883.

(51) Int. Cl.
*C12M 1/35* (2006.01)
(52) U.S. Cl. .................................... 435/287.4
(58) Field of Classification Search ............... 435/287.4
See application file for complete search history.

(56) References Cited

U.S. PATENT DOCUMENTS

| | | | |
|---|---|---|---|
| 4,087,326 A | 5/1978 | Kereluk | |
| 4,478,946 A | 10/1984 | Van der Merwe et al. | |
| 5,077,210 A | 12/1991 | Eigler et al. | |
| 5,436,147 A | 7/1995 | Pegg et al. | |
| 5,739,004 A | 4/1998 | Woodson | |
| 5,795,730 A | 8/1998 | Tautvydas | |
| 5,856,118 A | 1/1999 | Dalmasso | |
| 5,942,408 A | 8/1999 | Christensen et al. | |
| 5,955,335 A | 9/1999 | Thust et al. | |
| 6,121,012 A | 9/2000 | Falkowski et al. | |
| 6,159,695 A | 12/2000 | McGovern et al. | |
| 6,528,264 B1 | 3/2003 | Pal et al. | |
| 7,416,883 B2 * | 8/2008 | Cregger et al. | 435/287.4 |
| 7,741,107 B2 * | 6/2010 | Cregger et al. | 435/287.4 |
| 2003/0027242 A1 | 2/2003 | Felkner et al. | |
| 2009/0197316 A1 * | 8/2009 | Johnson et al. | 435/187 |

FOREIGN PATENT DOCUMENTS

| | | |
|---|---|---|
| GB | 1 316 808 | 5/1973 |
| WO | WO 94/28164 | 12/1994 |
| WO | WO 2006/034064 | 3/2006 |

OTHER PUBLICATIONS

Thermo Scientific, Pierce Protein Research Products EDC fact page, Jul. 13, 2010 print date.*

* cited by examiner

*Primary Examiner* — Ralph Gitomer
(74) *Attorney, Agent, or Firm* — Hudak, Shunk & Farine Co. LPA

(57) ABSTRACT

A biological indicator for monitoring the effectiveness of a sterilizing, disinfecting treatment or process. A compound or condition is disclosed which comprises a substrate containing functional groups residing on a surface thereof, said functional end groups being desirably free of silicon linking groups. The functional end groups are desirably in the form of a monolayer of a uniform distribution and of a selected quantity. Various types of microorganisms, such as spores, fungi, mycobacteria, vegetative bacteria, protozoa, and/or etiological agents are covalently bonded to the functional end groups through a zero-length crosslinking agent and thus form a uniform number and distribution of microorganisms and/or etiological agent indicators on a surface of the substrate. After being subjected to sterilization, disinfection, or other similar treatments or processes, along with various articles such as instruments, the indicator can be cultured in an appropriate medium to determine the effectiveness of the sterilization, disinfection, or other similar process.

8 Claims, No Drawings

US 7,960,169 B2

BIOLOGICAL INDICATOR

CROSS REFERENCE

This application is a continuation application of U.S. patent application Ser. No. 12/082,642, filed Apr. 11, 2008. and now U.S. Pat. No. 7,741,107, issued Jun. 22, 2010, for BIOLOGICAL INDICATOR, which is a continuation of U.S. patent application Ser. No. 11/135,719, filed May 24, 2005, and now U.S. Pat. No. 7,416,883 issued Aug. 26, 2008 which is hereby fully incorporated by reference.

BACKGROUND OF THE INVENTION

1. Field of the Invention

The invention relates to a biological sterile indicator for monitoring sterility or disinfection, etc., having a carrier surface containing functional groups which are covalently bonded to one or more microorganisms through a crosslinking reagent. The indicator desirably contains a uniform and consistent microorganism population which can be utilized in evaluating various sterilizing treatments of medical devices and accessories, instruments, solutions, surfaces, clothes, and the like, to indicate the degree or success of sterilization with respect to articles that are to be reused or terminally sterilized.

2. Description of the Prior Art

Biological indicators are used to test and/or determine the effectiveness of sterilization processes. A typical biological indicator contains a calibrated population of microorganisms having a high resistance to the sterilization process under investigation. After exposure to the sterilization process, the biological indicators are incubated in a culture medium to encourage growth of any remaining viable microorganisms. Self-contained biological indicators contain the culture medium within the indicator, typically in a frangible vial. Spore strip biological indicators are combined with a separate container of culture medium after the monitored sterilization process. Subsequent microbial growth, as demonstrated by a color change or turbidity of the growth medium, is an indication that the sterilization process was ineffective.

Bacterial spores are typically favored for biological indicators due to the fact that microbial spores are accepted as being more resistant to sterilization processes than most other types of microorganisms, and thus it is assumed that a sterilization process that will kill microbial spores will also kill any other contaminating microorganism.

The choice of bacterial spores is dependent upon the sterilization mode, sterilization type, and technique to be evaluated. For example, *Geobacillus stearothermophilus* spores are used to monitor sterilization systems employing moist heat, peracetic acid, hydrogen peroxide, and other peroxy compounds in both the liquid and vaporous state because these indicator spores are highly resistant to oxidative chemistries. Similarly, *Bacillus subtilis* spores are employed to monitor ethylene oxide sterilization, and dry heat sterilization systems.

The microorganisms are generally supported on a carrier or substrate, such as a strip or disk. The substrate is formed from a material which is compatible with the sterilization process and does not contain additives which may influence the sterility assessment. Materials such as filter paper, chromatography paper, blotter paper, glass fibers, polymer plastics, ceramics, stainless steel, and metaloxide articles are often used as a substrate or carrier.

To distribute the organisms on the substrate, a suspension of microorganisms in water or alcohol is conventionally pumped to a needle which is suspended over a web of the paper or other substrate material. The paper is moved under the needle at a constant rate, causing a trail of suspension to form on the paper as it passes beneath the needle. Alternatively, the suspension is manually transferred by use of a micropipette to the substrate. The web of impregnated paper is then cut to the appropriate size for use as the indicator, typically as test strips or test disks.

As well as the necessity for a controllable quantity of the microorganism to the substrate surface, it is important that the microorganism be sufficiently immobilized on the surface of the substrate. Various types of linkages of the microorganism to the substrate surface have been proposed, including hydrophobic and electrostatic interactions, ion exchange, and van der Waal's forces. U.S. Pat. No. 4,478,946, relates to the adsorption of nonfunctional proteins to a surface and the employment of crosslinking agents to covalently attach functional proteins to adsorbed non-functional proteins. However, such immobilization techniques often provide less than desirable attachment, especially in aqueous environments. U.S. Pat. No. 5,077,210 relates to active agents such as proteins covalently immobilized on substrates carrying hydroxyl groups. A silane is bound to the substrate and coupled to a heterobifunctional crosslinker at one functional group leaving a free functional group, different than the first group, to which a protein is bound while retaining high protein functionality. The silane has a functional group which reacts with the hydroxyl group of the substrate and a thiol terminal group which reacts with a functional group of a heterobifunctional crosslinking agent which contains a succinimide group that reacts with an amino group of the active agent.

SUMMARY OF THE INVENTION

A biological indicator for determining whether a sterilization, disinfection, or other such biocidal treatment was effective with regard to complex organic living organisms, comprises a substrate inherently containing functional groups thereon or added thereto, or a self-assembled surface layer thereon such as a functional group containing monolayer (SAM). The functional groups include hydroxyl groups, halide groups, amine groups, and the like, and desirably exclude thio groups. In a preferred embodiment, a crosslinking agent such as a heterobifunctional compound is utilized which provides a covalent linkage of a microorganism indicator such as a spore, vegetative organism, or an etiological agent to the functionalized substrate surface. In such an embodiment, the microorganism indicator is tightly bound to either the surface layer or preferably to the substrate not having any surface layer thereon, and is very difficult to remove by washing, fluid turbulence, and the like.

In another embodiment, the inherent functional hydroxyl groups of a substrate such as glass can be utilized. In this embodiment, the microorganism indicator or etiological agent is bound to the hydroxyl functional surface as by way of, but not limited to, a physical, electronic, etc. manner or through hydrogen bonding, but not by a covalent bond.

In a less desired embodiment, a functional group is added to the substrate surface through the use of an organic silane coupling agent wherein two different functionalized groups are generally utilized. In this embodiment, the microorganism indicator is bound to the silane coupling agent as through a physical, electronic, etc. manner, but not by a covalent bond.

In either embodiment, the functional agent is applied in a uniform and consistent manner thereby ensuring that the microorganism population thereon will also be uniform and consistent.

The biological indicators are generally utilized to indicate whether a sterilization, disinfection, or other such biocidal treatment of various articles such as surgical instruments have been effective so that the articles can be reused.

A biological indicator for monitoring sterility; comprising: a substrate; a surface layer containing functional end groups residing on said substrate, said surface layer being substantially free of any silicon linking atoms; a microorganism indicator; and a crosslinking reagent covalently bonded to said surface layer functional groups and covalently bonded to said microorganism indicator.

A biological indicator, comprising: a substrate and optionally a surface layer residing on said substrate, said substrate or said optional surface layer containing functional groups; an etiological agent comprising a bioterrorism agent, a clinically relevant organism, a resistant strain of bacteria, or a subcellular constituent, or combinations thereof; and a crosslinking agent covalently bonded to said substrate functional group or to said optional surface layer functional group and covalently bonded to said etiological agent.

DESCRIPTION OF THE INVENTION

A biological indicator is described that is suitable for monitoring and/or determining the biocidal effectiveness of a sterility, disinfection, or deactivation process of microorganisms, Prions, etiological agents, and the like, which are generally highly resistant to such treating processes. While spores, e.g. endospores, are the preferred test microorganism because they generally have a high resistance to many sterile processes, other microorganisms including fungi, mycobacteria, vegetative bacteria, and protozoa, can also be used in place of spores. Desirably, the microorganisms have sulfur end groups thereon and if not, they can be thiolated to contain sulfur end groups. Examples of endospores include *Geobacillus stearothermophilus, Bacillus subtilis, Bacillus subtilis globigii, Clostridium sporogenes, Bacillus cereus*, and *Bacillus circulans*. Examples of fungi include *Aspergillus niger, Candida albicans, Trichophyton mentagrophytes*, and *Wangiella dermatitis*. Examples of mycobacteria which can be utilized in the present invention include *Mycobacterium chelonae, Mycobacterium gordonae, Mycobacterium smegmatis*, and *Mycobacterium terrae.*

Examples of vegetative bacteria include *Aeromonas hydrophila, Enterococcus faecalis, Streptococcus faecalis, Enterococcus faecium, Streptococcus pyrogenes, Escherichia coli, Klebsiella* (pneumoniae), *Legionella pneumophila, Methylobacterium, Pseudomonas aeruginosa, Salmonella choleraesuis, Helicobacter pylori, Staphylococcus aureus, Staphylococcus epidermidis*, and *Stenotrophomonas maltophilia*. With respect to vegetative bacteria, vegetative cells and or their constituent parts can be affixed to a solid support matrix by the same mechanism(s) and survive drying and storage by means of deposition in the presence of one or more of a variety of excipients. Excipients are a broad class of generally inert compounds that are used to stabilize labile entities. A subclass of excipients includes the carbohydrates and notably oligo and polymeric saccharides. One example of such a compound is the disaccharide trehalose. High concentrations of trehalose in the tissues of certain organisms allow them to survive in a state of water deficiency and have also been shown to revive functional cellular components after dehydration. In fact, trehalose is known to provide stability to membranes and other macromolecular structures essential to the viability of a cell under extreme environmental conditions (i.e. freeze drying). Other stabilizing excipient compounds include (but are not limited to) simple sugars, e.g. sucrose, glucose, maltose, long chain polymers e.g. dextrans, starch, agarose and cellulose. Other non-carbohydrate based excipients might also include proteins, phosphonates, buffering agents, waxes, lipids, oils or other hydrocarbon based materials.

Examples of protozoa include *Giardia lamblia* and *Cryptosporidium parvum.*

Spores are preferred in the present invention because they are highly resistant to sterilization, etc., processes.

In addition to monitoring and/or determining the effectiveness of various treatments or processes with regard to sterilizing, etc. endospores, fungi, etc., the indicators of the present invention can also be utilized with regard and/or determining the effectiveness of a sterile or disinfecting treatment or process.

Etiological Agents and Other Non-Simulative Agents

Etiological agents include bioterrorism agents, clinically relevant agents, sub-cellular components, and emerging resistant strains of bacteria. In addition to the simulative organisms selected on the basis of their acceptance as representing a 'most resistant' nature (e.g. *Geobacillus stearothermophilus*) and other microorganisms set forth above, non self-replicating agents and sub cellular components or products of cells can be selected based on their clinical significance or because of their use as agents of bioterrorism. These organisms are often comprised of strains which may now have resistance to normal means of antibiotic treatment or chemical disinfection due to natural or manmade modifications. Examples of the former type minimally include VRE's (Vancomycin Resistant *Enterococci*), MSRAs (Methicillin Resistant *Staphylococcus aureus*), and *Mycobacterium cheloni*. These clinically significant organisms are particularly of interest because the VRE's and MRSAs represent organisms which have developed resistance to their typical therapeutic countermeasures (antibiotic resistance) and *M. cheloni* exemplifies organisms that have developed resistance to some heretofore effective modes of disinfection (glutaraldehyde resistance). There are also a number of emerging etiological agents of significance for which there may not yet be a simulative alternative, which may represent a special risk or challenge to therapeutic course of action or disinfection. One such example is prions. Prions are not living organisms, per se, but their function as disease causing agents are related to their structure and this structure/function relationship can be employed to determine their relative infectivity. Other non-autonomous agents (e.g. viruses) as well as sub cellular elements and proteinaceous prions are contemplated in the present invention.

Etiological agents which can be used as bioterrorism agents or diseases include anthrax (*Bacillus anthracis*), botulisum (*Clostridium botulinum* toxin), *brucella* species (brucellosis), *Burkholderia mallei* (glanders), *Burkholderia pseudomallei* (Melloidosis), *Chlamydia psittaci* (psittacosis), cholera (*Vibrio cholerae*), *Clostridium perfringens* (Epsilon toxin), *Coxiella burnetii* (Q fever), emerging infectious diseases such as nipah virus and hantavirus, *Escherichia coli* O157:H7 (*E. coli*), food safety threats (e.g. *salmonella* species), *Francisella tularensis* (tularemia), plague (*Yersinia pestis*), ricin toxin from *Ricinus communis* (castor beans), *Rickettsia prowazekii* (typhus fever), *Salmonella typhi* (typhoid fever), *shigella* (shigellosis), smallpox (*Variola major*), *Staphylococcal enterotoxin* B, *Vibrio cholerae* (cholera), *Viral encephalitis* (alphaviruses [e.g. Venezuelan equine encephalitis, eastern equine encephalitis, western equine encephalitis]), viral hemorrhagic fevers (filoviruses [e.g. Ebola, Marburg] and arenaviruses [e.g. Lassa, Machupo]), water safety threats (e.g. *Cryptosporidium parvum*), and *Yersinia pestis* (plague), or combinations thereof.

The test microorganism can be a single species or a combination of species. Where a combination of species is utilized, for typical sterilization processes for medical devices, the preferred organisms will most often be a combination of *Geobacillus stearothermophilus* and *Bacillus subtilis*.

A solid substrate is preferably utilized as the spore carrier material. The substrate can be any inorganic material such as silicon including crystalline silicon; various types of glasses including soda-lime, borosilicate glass, phosphate glass, borophosphate glass, boroaluminosilicate glass, and the like having any shape or form such as a sheet, fiber, bead, ballotini; various ceramics which can be defined as earthly raw materials in which silicon and its oxide and complex compounds known as silicates occupy a predominate portion and which have been heated to high temperatures such as structural clay products including tile and terra cotta, various porcelains, porcelain enamels, and the like; metal such as palladium, platinum, iron, copper, gold; various inorganic substrates containing metalized surfaces such as those immediately set forth, or various metal oxides of groups 4 through 14 of the Periodic Table including titanium oxide, zirconium oxide, iron oxide, copper oxide, aluminum oxide, silica such as quartz, sapphire, and the like.

Another group of substrates which can be utilized are various organic compounds including cellulose in various forms such as paper, filter paper, cardboard, and the like. Various polymers can be exemplified by, but not limited to, acrylic polymers including acrylic acid and acrylate polymers, various polyolefins such as polyethylene and polypropylene, polyvinyl alcohol polymers; polystyrene; and the like. The above noted substrates can also be composites of the above noted compounds.

The substrates can be electronically and/or physically modified by plasma, electron beams, gamma radiation, photo activation, and the like. Such treatments can use existing functional groups, add functional groups, or make assessable inherent groups (i.e. active), on the substrate surface such as hydroxyl groups. Normally, at least part of the exposed surface of the substrate will be planar, although curved surfaces can be treated in accordance with the present invention; e.g., the substrate surface can be formed on the inside, or outside surface of a test tube or from a multi-well plate or the outside of a bead or container. While the substrate is preferably solid, it can be partially porous or porous.

The substrates can exist in a large variety of forms so long as they provide an exposed surface. Examples of suitable forms include fibers, wires, wafers, discs, sheets, microscope slides, crystallizing dishes, closed absorption cells, glass media ampoules, and the like. Preferred substrates include various forms of cellulose such as paper, glass fibers, alkaline earth aluminoborosilicate glass, polystyrene, and the like.

The substrates of the present invention can naturally or inherently contain functional groups thereon, e.g. various glasses often contain hydroxyl groups or amine groups. Alternatively, a separate surface layer containing functional groups can reside or exist on the substrate as in the form of a monolayer such as a SAM (self-assembled monolayer method), which is well known to the art and to the literature. The inherent or additional layer of functional groups comprise hydroxyl, amine, carboxylic acid, carbonyl, various halides such as chlorine or bromine, and various alkenes containing a total of from about 2 to at least about 20 carbon atoms. Thio groups are generally avoided.

It is an important aspect of the present invention to utilize various different types of crosslinking agents to covalently bond the microorganism indicator to the substrate. The crosslinking agent can have functional groups which are the same or different and numerous types of functional groups exist and may fall into more than one category such as various amine compounds including primary, secondary, and tertiary amines, various imines, various imides including aniline, imidyl esters of carboxylic acids, hydroxyl, carboxylic acids, alkenyl groups having from 2 to at least about 20 carbon atoms, halides such as chlorine or bromine, nitroaryl halides, alkoxy groups having a total of from 1 to at least about 20 carbon atoms, anhydrides, aldehydes, cyanos, various sulfur containing groups such as thios, disulfides or dithios and the like. Preferred reactive end groups of the crosslinking agents generally include the various amines with primary amines being preferred, thio or other sulfur containing groups, carboxyl, and hydroxyl. Common compounds containing amines therein include succinimidyl esters, maleimides, azides, and iodoacetamides.

Suitable crosslinking reagents include homobifunctional crosslinking reagents, heterobifunctional crosslinking reagents, trifunctional crosslinking reagents, zero-length crosslinking reagents, and photoreactive crosslinking reagents. Heterobifunctional crosslinking reagents are preferred.

Examples of homobifunctional crosslinking reagents include various amines such as Bis[sulfosuccinimidyl] suberate (BS3), and 3-[2-aminoethyldithio] propionic acid HC1 (AEDP).

Examples of heterobifunctional crosslinking reagents include N-succinimidyl 3-(2-pyridyldithio) propionate (SPDP), N-sulfosuccinimdyl6-[3'(2-pyridyldithio)-propionamido] hexanoate (Sulfo-LC-SPDP), N-succinimidyl 6-[3' (2-pyridyldithio)-propionamido] hexanoate (LC-SPDP), N-succinimidyl acetylthioacetate (SATA), N-succinimidyl trans-4-(maleimidylmethyl)cyclohexane-1-carboxylate (SMCC), N-sulfosuccinimidyl trans-4-(maleimidylmethyl)cyclohexane-1-carboxylate (Sulfo-SMCC), N-Succinimidyl (4-iodoacetyl)aminobenzoate (SIAB), N-Sulfosuccinimidyl (4-iodoacetyl)aminobenzoate (Sulfo-SIAB), m-Maleimidobenzoyl-N-hydroxysuccimide ester (MBS), Succinimidyl 4-[p-maleimidophenyl] butyrate (SMPB), Sulfosuccinimidyl 4-[p-maleimidophenyl] butyrate (Sulfo-SMPB), N-(a-Maleimidoacetoxy) succinimide ester (AMAS), Succinimidyl-6-[β-maleimidopropionamido]hexanoate (SMPH), N-Succinimdyl iodoacetate (SIA), N-κ-Maleimidoundecanoic acid (KMUA), and Succinimidyl 3-[bromoacetamido] propionate (SBAP). Other crosslinking agents include N-Hydroxysuccinimide (NHS), N-Hydroxysulfosuccinimide (Sulfo-NHS), 3-[2-Aminoethyldithio] propionic acid HCl (AEDP) (can also be a homobifunctional crosslinking reagent), Methyl N-succinimidyl adipate (MSA), N-β-Maleimidopropionic acid (BMPA), N-[κK-Maleimidoundecanoic acid]-hydrazine (KMUH), and N-[β-Maleimidophenyl propionic acid] hydrazide•TFA (BMPH), and N-[p-Maleimidophenyl] isocyanate (PMPI).

An example of a trifunctional crosslinking reagent is Tris-succinimidyl aminotriacetate (TSAT).

Examples of zero-length crosslinking reagents include 1-Ethyl-3-[3-dimethylaminopropyl]carbodimide hydrochloride (EDC).

Examples of photoreactive crosslinking reagents (i.e. react specifically with available nucleophiles upon UV illumination) include amine reactives such as 4-azido-2,3,5,6-tetrafluorobenzoic acid, succinimidyl ester (ATFB, SE); 4-azido-2,3,5,6-tetrafluorobenzoic acid STP ester, sodium salt (ATFB, STP ester); Benzophenone-4-isothiocyanate; 4-benzoylbenzoic acid, succinimidyl ester; N-5-Azido-2-nitrobenzoyloxysuccinimide (ANB-NOS); Sulfosuccinimidyl 2-[m-azido-o-nitrobenzamide]ethyl-1,3'-dithiopropionate (SAND); N-Succinimidyl-6-[4'-azido-2'-nitrophenylamino] hexanoate (SANPAH); Sulfosuccinimidyl-6-[4'-azido-2'-nitrophenylamino]hexanoate (Sulfo-SANPAH); and Succinimidyl-[4-(psoralen-8-yoloxy)]butyrate (SPB); thiol reactives include N-([2-pyridyldithio]ethyl)-4-azidosalicylamide; and Benzophenone-4-maleimide; and carbonyl reactives include 4-azido-2,3,5,6-tetrafluorbenzylamine hydrochloride.

Still other crosslinking reagents include N-gamma-maleimidobutyryloxy succinimide ester, 1,3-bismaleimido propane which has the formula

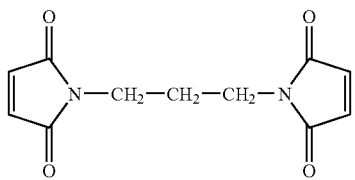

the N-hydroxysuccinimide ester of N-(4)-carboxycyclohexylmethyl)-maleimide, and the N-hydroxysuccinimide ester of 3(2-pyridyl-dithio)-propionic acid having the formula

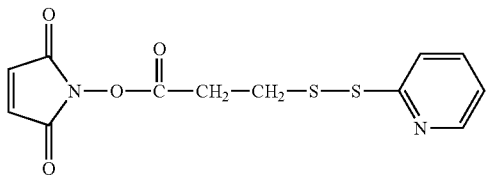

The various homobifunctional, heterobifunctional, trifunctional, zero-length, and photoreactive crosslinking reagents will thus react through one end group with the substrate or separate surface layer functional compound to form a covalent bond therewith whereas the remaining one or more functional end group(s) will react with a microorganism indicator or etiological agent and also form a covalent bond therewith. The order of reaction is not important since the crosslinking agent can first be reacted with a functional group of the surface or of a surface layer and subsequently with the microorganism, or initially with the microorganism and subsequently with the surface or surface layer functional group.

It is an important aspect of the invention to bond the microorganism indicator to the substrate through strong covalent bonds of at least about 10, desirably from about 10 to about 150, and preferably from about 25 to about 125 kilocalories per mole. Such strong bonds or anchorages of the microorganism indicator or etiological agent to the substrate are resistant to adverse or turbulent conditions associated with washer-disinfectors and/or liquid chemical sterile processes. In other words, the biological indicators of the present invention are highly resistant to being washed away or separated from the substrate as from jet spray impingement, turbulent hydrostatic forces, and the like.

The biological indicator of the present invention is prepared by applying a layer of crosslinking reagents to the substrate or to the substrate-separate layer laminate containing a functional group thereon. Preferably, the functional groups are substantially free of or contain no silicon linking atoms. Silicon linking atoms occur when a functionalized silane coupling agent is utilized. By substantially free it is meant that generally less than about 10%, desirably less than about 5% and preferably less than about 2 or 3%, or nil, that is none, of the functional groups are bonded to the substrate through an intermediate silicon atom. The substrates are also substantially free of proteins, partially hydrolyzed proteins and peptides. The amount of any such proteins, etc. if they exist is low such as generally less than about 10%, desirably less than about 5% and preferably less than about 2% or 3% of the functional groups which are bonded to the substrate. Depending upon the type of the above noted functional groups contained on the substrate or the surface layer, a crosslinking reagent is utilized having at least one end group which readily reacts therewith and forms a covalent bond. For example, if the substrate surface has an amine functional group, one of the functional groups of the crosslinking reagent such as a heterobifunctional reagent will readily react therewith such as an aldehyde, an imide, a carboxyl group, an amidyl ester of a carboxylic acid, an anhydride, and the like. One such method relates to utilizing the crosslinking reagent in a buffer such as a phosphate buffer at relatively neutral conditions, for example a pH of from about 6 to about 8, for a suitable amount of time to permit a covalent bond to be formed with the functional group of the substrate. Excess crosslinking reagent can be removed in any conventional manner as by rinsing or washing, or the like.

The remaining one or more end groups of the crosslinking reagent is a functional group that readily reacts with the microorganism indicator, or etiological agent and forms a covalent bond therewith. Thus, the microorganism indicator, etiological agent, or disease causing agent or stimulant, etc., are covalently bonded to the substrate functional group through the crosslinking reagent. Such functional groups, as noted above, that react with the microorganism include a halogen, a melamine derivative, a thio group, a maleimide, a malamide, etc. Should the remaining functional group of the crosslinking reagent be blocked as by a pyridine group, the same can be removed by utilizing a common reducing agent. Examples of suitable reducing agents include dithiothreitol (DTT), β-mercaptoethanol, DMF, DMSO, lithium aluminum hydride, sodium borohydride, and the like. In a preferred embodiment of the present invention, the heterobifunctional agent is SPDP which upon reduction of the compound removes the pyridine group leaving a hydrogen sulfide group which readily reacts and covalently bonds to the sulfur present in the thio group of the spore thereby immobilizing the spore to the substrate surface.

Since the preferred microorganism of the present invention is a bacterial spore, and since the spore generally contains sulfur end groups thereon, it exemplifies a desired embodiment of the invention. Should the spore or microorganism not contain a sulfur end group, it can be thiolated before reaction with the crosslinking agent. Thiolation of microorganisms is known to the art and to the literature.

The various one or more crosslinking reagents can be reacted in a variety of ways such as at room temperature, at elevated temperatures, by radiation such as ultraviolet light, and the like.

An important aspect of the present invention is the uniform and/or consistent population of microorganism indicators or etiological agents on the substrate such that a low standard deviation is or combinations thereof; attained such as generally about 50% or less, desirably about 25% or less, and preferably about 10% or less based upon one area, for example, a cm$^2$ as compared to another area on the substrate. The uniform distribution of a microorganism indicator or etiological agent is prepared as by suspending a selected spore microorganism such as in an aqueous solution, generally water or solvent. Solvents can include ethanol, methanol, and other alcohols, with ethanol being the preferred. It should be understood, however, that the spores can be suspended in a wide variety of solutions, so long as the viability and resistance properties of the spores are not compromised.

Alternatively, the above-noted crosslinking reagents can be initially reacted with one or more types of microorganism indicators, or etiological agent, and the like, and then subsequently applied in an aqueous solution or solvent to a functional group containing substrate whereupon the crosslinking agent is covalently bonded thereto.

The prepared substrate having either an inherent functional group or functional groups provided by a self-assembled monolayer (SAM) which is covalently bonded to a crosslinking reagent is then inoculated with a microorganism, such as a spore suspension at a predetermined, particular concentration. The concentration of the spore suspension will vary, depending on the application requirements and desired rate of application to the substrate, but will generally be from about $10^4$ cfu/ml to about $10^9$ cfu/ml. Inoculation of the spore solution onto the carrier is accomplished by immersing or dipping the surface into the spore solution, pipetting, spraying, or printing a fixed volume of suspension onto the substrate. The actual amount of microorganism deposited or residing on the biological indictor will be from about $10^4$ to about $10^7$ cfu/ biological indicator. Where the substrate is generally flat such as a closed adsorption cell or microscope slide, the entire surface of the carrier is covered. Where the substrate is generally curved surface, such as a glass media ampoule, only an end portion or the entire surface is covered.

The inoculated substrate is then dried at ambient temperatures of from about 17° C. to about 25° C. for a period of time from about 1 min to about 30 min. or longer, or at elevated temperatures to reduce drying times. Following inoculation of the carrier, the carrier is rinsed with water or a solvent to remove spores that are not tightly bonded to the surface. The substrate may then be inspected visually utilizing photo-optimetric instruments such as an optical or scanning probe microscope to determine uniformity of the microorganism indicator population on the carrier surface. The population of the carrier surface can also be enumerated by titering macerated or sonicated samples, or by other means known to those skilled in the art.

In lieu of microorganism indicators such as spores, various etiological agents can be applied in a similar manner to the substrate to achieve a desirable concentration on the surface.

Due to the fact that substrates or surface layers can be made having uniform and consistent concentrations of functional groups thereon which are then covalently bonded via the crosslinking reagent to the microorganisms or etiological agents, they are strongly adhered to the substrate with very little loss, if any, due to turbulent and/or chemical sterile treatments or processes. The microorganisms such as the spores or etiological agent thus serve as a very effective biological indicator as to the effectiveness of the sterilization of various articles. For example, the biological indicators of the present invention are most useful with liquid chemical-type sterilization processes but can also be utilized in sterilizing processes such as steam, chemical, radiation, vapor phase, etc. for sterilizing various articles set forth below. Upon completion of the sterilizing cycle, the one or more biological indicators are incubated in a manner well known to the art and to the literature. If any of the microorganisms, for example spores, or etiological agents have survived the sterilizing process, they will grow during incubation under the appropriate incubation conditions known to those skilled in the art. The presence of any growth is an indication that the sterilization cycle may not have been successful. Thus, after incubation of the biological indicators, the disinfection or degree of sterility is determined in the conventional manner. The end result is often determined by the nature of the articles being sterilized with a log reduction of at least from about 4 to about 12, and preferably at least about 5 or about 6 to about 8 or about 9. A log reduction of 6 means that one or less microorganisms in 1,000,000 remain following exposure to a sterilization process.

The type of microorganism or spore, or etiological agent utilized in the biological indicator can often be the same as the specific organism sought to be destroyed. For example, with regard to biological warfare agents, if a composition or a container is thought to contain anthrax, an anthrax spore can be utilized so upon completion of the sterilization process, it can be determined whether or not the process was effective in destroying the anthrax indicator.

Articles which can be subject to sterilization utilizing a biological indicator of the present invention are numerous and comprise instruments including surgical instruments, equipment including tubing as for the transportation of medical and pharmaceutical compounds, compositions such as various powders, mixtures, solutions, cloth, and whenever an indication of a sterilizing or disinfecting process is sought.

The function and advantage of the embodiments of the present invention will be more fully understood from the examples below. The following actual examples are intended to illustrate the benefits of the present invention, but do not exemplify the full scope of the invention.

Example 1A

A substrate is utilized containing an amine terminated surface, whether manufactured with the functionality such as a glass or a polystyrene substrate, or modified using a self-assembled monolayer with the desired end group or treated by some physical or chemical means to release or make accessible functional groups. A heterobifunctional crosslinking reagent, N-succinimidyl 3-(2-pyridyldithio) propionate (SPDP), is reacted to the amine terminated surface in phosphate buffered saline for 30-60 minutes (a 20 mM SPDP stock solution is made in either DMSO or EtOH) at temperatures preferably between 17° C.-40° C. All excess SPDP is removed by rinsing in phosphate buffer. The surface is then reduced using dithiothreitol (DTT) for approximately 30 minutes. *Geobacillus stearothermophilus* spores are then reacted with the reduced surface for a length of time from about 1 second to about 18 hours. Moreover, the spore is covalently bonded to the crosslinking agent which in turn is covalently bonded to the amine functional group on the substrate.

Example 1B

Thiolation of a Spore

A spore solution of $10^6$ to $10^9$ cfu/mL is formulated with a PBS solution. A 120 μL aliquot of 20 mM SPDP is added to 0.5 mL of the spore suspension. (The solutions can be scaled up as appropriate.) The SPDP is then reacted with the spores for a period of 1 second to about 2 hours, with between 1 second and 30 minutes being preferred. The amine reactive group of the SPDP, N-hydroxysuccinimide (NHS) will react with available amines in the proteins of the spore coat. The unreacted SPDP is then removed using typical methods such as dialysis, filtration, or both, or other means known to those skilled in the art. Following separation of the unreacted SPDP, the newly thiolated spores are brought in contact with a surface that has been pre-modified with SPDP (following the same methodology as used in other examples) and subsequently reduced. The spore will then react with the surface creating a covalently linkage through a disulfide bound.

Example 2

No Reducing Agent

Using a substrate with native hydroxyl functional groups (or a polymeric surface that has been treated with gas plasma to create hydroxyl functionalities at the surface), the heterobifunctional reagent, N-(p-Maleimidophenyl) isocyanate (PMPI), is reacted to the surface containing hydroxyl groups in a non-hydroxylic buffer at alkaline pH for 30 minutes (a PMPI stock solution is made in either DMSO or DMF at an approximately 10-fold molar excess over the concentration of hydroxyls present at the surface). The isocyanate end group of the PMPI is then reacted with the hydroxyl molecules on the surface of the substrate to form urethane linkages. The sulfhydryl groups present on the spores *Geobacillus stearothermophilus* are then reacted with the maleimide functional end of the crosslinker at a neutral pH for a period of 2 hours at room temperature. The heterobifunctional crosslinking reagent is covalently bonded to the spores and to the hydroxyl groups of the substrate.

Example 3

No Reducing Agent

A substrate having either native double bonds, such as vinyl groups near the surface or a surface treated to create double bonds, is submerged in a sodium phosphate solution of pH 7-9 in the presence of a 10% solution of 10 mM N-Succinimidyl-6-[4'-azido-2'-nitrophenylamino]hexanoate (SANPAH) in either DMSO or DMF. The sample (substrate and solution) is exposed to UV light at a wavelength of 300-460 nm (desirably between 300 nm-370 nm) for typically less than a minute. The nitrophenyl azide group of the SANPAH forms a nitrene group which in turn initiates an addition reaction with the double bonds on the surface of the substrate. In a phosphate buffer at pH 7, a spore *Geobacillus stearothermophilus* suspension (concentration of $10^7$ cfu/ml) is brought in contact with the modified surface for a period of 60 minutes at room temperature. The NHS esters react with the primary amino groups to form stable amide bonds. The SANPAH crosslinking agent is covalently bonded to the spores and to the vinyl group, located on the surface of the substrate.

In another embodiment of the present invention, a functionalized silane coupling agent is utilized to add a functional group to the substrate with the functional group subsequently being directly attached to the microorganism indicator with no intervening crosslinking reagent. Accordingly, no covalent bond is formed between the substrate functional group and the microorganism such as a spore, but rather a physical or other type of non-covalent bond is formed. The functionalizing coupling agent can have the formula $(FR)_n SiX_{4-n}$ where n equals from 1 to 3, and desirably from 1 to 3. R is an organic compound such as an alkyl having from 1 to about 20 carbon atoms and desirably from 2 to about 18 carbon atoms, and preferably from 3 to about 16, or an aromatic compound having from 6 to about 20 carbon atoms, and desirably from 6 to about 15 carbon atoms, or combinations thereof such as an alkylaryl, and an arylalkyl, and the like. X is a halide, such as a chloro or a bromo group with chlorine being preferred, or an alkoxy group, $OR^1$, wherein $R^1$ is an alkyl having from 1 to about 10 carbon atoms, and preferably from 1 to 2 carbon atoms. Accordingly, a large number of silane coupling agents can be utilized and representative examples include propyltrimethoxysilane, butyltrimethoxysilane, propyltriethoxysilane, butyltriethoxysilane, propyltrichlorosilane, propyltribromosilane, butyltrichlorosilane, butyltribromosilane, 11-hexadecyltrichlorosilane, 15-pentadecenyltrichlorosilane, 11-bromoundecyltrichlorosilane, monochlorosilane, dichlorosilane, and the like. The silane coupling agent functional group, F, is a compound which can be attached to the bacteria, spore, etc. as through physical linkage. Suitable functional groups include thio compounds, amine compounds, carbonyl containing compounds, bromine compounds, epoxy compounds, carboxyl containing compounds, alkene compounds, and alkyne compounds, and the like, as well as derivatives thereof. Examples of functionalized silane coupling agents thus include 3-aminopropyltrimethoxysilane, 3-aminopropyltriethoxysilane, 3-mercaptopropyltrimethoxysilane, 3-mercaptopropyltriethoxysilane, 3-aminopropyltrichlorosilane, 3-mercaptopropyltrichlorosilane, and the like.

Since the various organic silanes generally have more than one X group and typically 3, they can crosslink with hydroxyl groups which inherently exist on some substrates such as glass and cellulose to form a two-dimensional mono-layer network of

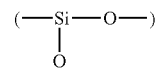

groups wherein the oxygen atoms are derived from the hydroxyl group bonded to the substrate surface. Naturally, a single type of functionalized silane coupling agent can be utilized or a mixture of two or more different types of functionalized silane coupling agents. The end result is the creation of a high density of microorganism indicators which are immobilized on the substrate surface.

The process of preparing the layer of the functionalized organosilane coupling agents to the substrate comprises applying the silane compound in a solvent which has been heated to about 60° C.-75° C. prior to deposition of the corresponding alkylsilane. Suitable solvents are any dry organic solvent, including aromatic hydrocarbons such as toluene, hexadecane, benzene, naphthalene, xylene, dry ketones such as acetone and the like, with hexadecane being preferred.

The microorganism indicator such as spores can be physisorbed to the surface through hydrophobic or electrostatic interactions between the functional molecules on the substrate surface and the proteins in the spore coat. The spores can also be chemisorbed to the surface using the amine groups present in the proteins.

Example 4

Silane Linking Agent

Samples of a substrate material containing a closed adsorption cell or a crystallizing dish are prepared by cleaning with a solution of sulfuric acid and hydrogen peroxide to remove any organic impurities on the surface. The substrate is then rinsed with copious amounts of water to remove any residual acid or peroxide.

The substrate is then soaked in a silane solution consisting of 1% hexadecyltrichlorosilane or 11-bromoundecyltrichlorosilane or 15-pentadecenyltrichlorosilane in hexadecane for approximately 30 seconds to 5 hours in a 60° C.-75° C. water bath. The substrate is then removed and rinsed with a nonpolar solvent to remove residual silane molecules.

To prepare the biological indicator, the functionalized substrate is submerged, or dipped, into approximately 5-100 mLs of a spore solution for a time between about 1 second and about 18 hours, with the preferred time between 1 second and 3 hours. Alternatively the functionalized substrate can be inoculated, sprayed, or printed with the spore suspensions. Following submersion, or dipping, in the spore solution, the substrate is left in ambient conditions (17° C.-25° C. and 1-30 minutes) to dry. Once dry, the biological indicating article is then rinsed with sterile water to remove any loosely attached spores. This rinse allows only the tenaciously attached spores to remain. The biological indicator is then dried again at ambient conditions and inspected to determine the number and distribution of the spore population.

Example 5

Silane Linking Agent

Samples of a glass substrate material are modified to contain an amine terminated surface thereon. The glass surfaces are cleaned using a solution of 30% hydrogen peroxide (35%) and 70% concentrated sulfuric acid. The amine functional surface is prepared by submerging the cleaned glass surface in a 1% solution of 3-aminopropyltrimethoxysilane in an anhydrous solvent, preferably hexadecane or acetone. The amine functional surface is soaked in a phosphate buffered saline solution containing a 20 mM SPDP stock solution in either DMSO or EtOH for a time of from about 30 minutes to about 60 minutes at a temperature between 17° C.-25° C. Excess SPDP is then removed by rinsing in phosphate buffer.

The substrate surface is then reduced using an acetate buffer solution containing 25 mg/ml dithiothreitol (DTT). The surface is soaked in the acetate/DTT solution for 30 minutes at a temperature of 17° C.-25° C. The surfaces are then rinsed with copious amounts of acetate buffer to remove any DTT.

To prepare the biological indicating article, the substrate with the heterobifunctional agents attached is submerged, into an appropriate volume of a spore solution for a time between about 30 seconds and about 20 hours. Following submersion, or dipping, in the spore solution, the substrate is left in ambient conditions [17° C.-25° C.] to dry.

Example 6

In yet another embodiment, hydroxyl functionalized surfaces, such as borosilicate glass, can be used to prepare the biological indicator. The functionalized substrate is submerged, or dipped, into approximately 5-100 mLs of a spore solution for a time between about 1 second and about 24 hours, with the preferred time between 1 second and 3 hours. Following submersion, or dipping, in the spore solution, the substrate is left in ambient conditions (17-25° C. and 1-30 minutes) to dry. Once dry, the biological indicating article is then rinsed with sterile water to remove any loosely attached spores. The rinse allows only the tenaciously attached spores to remain. The biological indicator is then dried again at ambient conditions and visually inspected to determine distribution of the spore population and the number of spores on a surface. A uniform spore population is obtained wherein the standard of deviation is approximately 25% or less.

While in accordance with the patent statutes, the best mode and preferred embodiment have been set forth, the scope of the invention is not limited thereto, but rather by the scope of the attached claims.

What is claimed is:

1. A biological indicator for monitoring sterility, comprising:
    a substrate;
    a surface layer containing functional groups residing on said substrate, said surface layer functional groups containing about 10% or less of any silicon linking atoms based upon the total amount of said surface layer functional groups;
    a plurality of microorganism indicators comprising an endospore, a fungi, a mycobacteria, a vegetative bacteria, a protozoa, or any combination thereof;
    a zero-length crosslinking agent having one functional end group covalently bonded to one of said surface layer functional groups and having another functional end group covalently bonded to one of said microorganism indicators so that a terminal and exposed microorganism indicator is present that is covalently bonded through said crosslinking agent to said surface layer, said surface layer having a plurality of said terminal and exposed microorganism indicators bound thereto that are capable of being sterilized by a sterilizing medium,
    wherein said plurality of said exposed and bound microorganism indicators covalently bonded to said surface layer have a uniform distribution, wherein the standard deviation of the distribution is about 50% or less based on one unit area of said surface layer as compared to another unit area of said surface layer; and
    wherein the zero-length crosslinking agent comprises 1-ethyl-3-[3-dimethyl-aminopropyl] carbodimide hydrochloride (EDC).

2. A biological indicator for monitoring sterility according to claim 1, wherein the amount of said silicon linking atoms is about 5% or less of the total amount of said functional groups bonded to said surface layer.

3. A biological indicator for monitoring sterility according to claim 2, wherein said surface layer functional groups comprise a hydroxyl, an amine, a carboxylic acid, a carbonyl, an alkene having from 2 to about 20 carbon atoms, a halide, or any combination thereof;
    wherein said endospore comprises *Geobacillus stearothermophilus, Bacillus subtilis, Bacillus subtilis globigii, Clostridium sporogenes, Bacillus cereus, Bacillus circulans*, or any combination thereof;
    wherein said fungi comprises *Aspergillus niger, Candida albicans, Trichophyton mentagrophytes, Wangiella dermatitis*, or any combination thereof;
    wherein said mycobacteria comprises *Mycobacterium chelonae, Mycobacterium gordonae, Mycobacterium smegmatis, Mycobacterium terrae*, or combinations thereof;
    wherein said vegetative bacteria comprises *Aeromonas hydrophila, Enterococcus faecalis, Streptococcus faecalis, Enterococcus facecium, Streptococcus pyrogenes, Escherichia coli, Klebsiella* (pneumoniae*Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, or any combination thereof; and wherein said protozoa comprises *Giardia lamblia, Cryptosporidium parvum*, or any combination thereof.

4. A biological indicator for monitoring sterility according to claim 3, wherein the amount of said silicon linking atoms is less than about 3%;
- wherein said endospore comprises *Clostridium sporogenes, Geobacillus stearothermophilus, Bacillus subtilis, Bacillus subtilis globigii*, or any combination thereof;
- wherein said mycobacteria comprises *Mycobacterium chelonae, Mycobacterium gordonae, Mycobacterium smegmantis, Mycobacterium terrae*, or any combination thereof; and
- wherein said vegetative bacteria comprises *Streptococcus faecalis, Streptococcus pyrogenes, Escherichia coli, Legionella pneumophila, Pseudomonas aeruginosa, Salmonella choleraesuis, Staphylococcus aureus*, or any combination thereof.

5. A biological indicator for monitoring sterility according to claim 4, wherein said surface layer functional group is an amine, a hydroxyl, or a combination thereof;
- wherein said endospore is *Geobacillus stearothermophilus, Bacillus subtilis globigii, Bacillus subtilis*, or any combination thereof;
- wherein the amount of silicon linking atoms is less than about 2%; and
- wherein said standard deviation is about 25% or less.

6. A biological indicator for monitoring sterility, comprising:
- a substrate and, optionally, a surface layer residing on said substrate, said substrate or said optional surface layer when utilized containing functional groups thereon, said functional groups containing about 10% or less of any silicon linking atoms based upon the total amount of said substrate or said optional surface layer functional groups;
- a plurality of etiological agent indicators comprising a bioterrorism agent, a clinically relevant disease-causing microorganism, a resistant strain of bacteria, a subcellular constituent, or any combination thereof; and
- a zero-length crosslinking agent having one functional end group covalently bonded to one of said substrate functional groups or to one of said optional surface layer functional groups and having another functional end group covalently bonded to one of said etiological agent indicators so that a terminal and exposed etiological agent indicator is present that is covalently bonded through said crosslinking agent to said substrate or to said optional surface layer, said substrate or said optional surface layer having a plurality of said terminal and exposed etiological agent indicators bound thereto that are capable of being sterilized by a sterilizing medium,
- wherein said plurality of said exposed and bound etiological agent indicators covalently bonded to said substrate or to said optional surface layer have a uniform distribution wherein the standard deviation of the distribution is about 50% or less based on one unit area of said substrate or said optional surface layer as compared to another unit area of said substrate or said optional surface layer, and
- wherein the zero-length crosslinking agent comprises 1-Ethyl-3-[3-dimethyl-aminopropyl]carbodimide hydrochloride (EDC).

7. A biological indicator for monitoring sterility according to claim 6, wherein said substrate or said surface layer functional groups comprise a hydroxyl, an amine, a carboxylic acid, a carbonyl, an alkene having from 2 to about 20 carbon atoms, a halide, or any combination thereof;
- wherein the amount of said silicon linking atoms is about 5% or less of the total amount of said substrate or said optional surface layer functional groups;
- wherein said etiological agent indicator comprises vancomycin resistant *Enterococci* (VRE), methicillin resistant *Staphylococcus aureus* (MRSA), *Mycobacterium cheloni*, viruses, proteinaceous prions, *Bacillus anthracis* (anthrax), *Clostridium botulinum* toxin (botulisum), *Brucella* spp. (brucellosis), *Burkholderia mallei* (glanders), *Burkholderia pseudomallei* (melloidosis), *Chlamydia psittaci* (psittacosis), *Vibrio cholerae* (cholera), *Clostridium perfringens* (Epsilon toxin), *Coxiella burnetii* (Q fever), nipah virus, hantavirus, food safety threats (*Escherichia coli* O157:H7, *Salmonella* spp.), *Francisella tularensis* (tularemia), *Yersinia pestis* (plague), *Ricinus communis* (ricin toxin), *Rickettsia prowazekii* (typhus fever), *Salmonella typhi* (typhoid fever), *Shigella* spp. (shigellosis), *Variola major* (smallpox), *Staphylococcal enterotoxin* B, alphaviruses (Venezuelan equine encephalitis, Eastern equine encephalitis, Western equine encephalitis), filoviruses (Ebola, Marburg), arenaviruses (Lassa, Machupo), water safety threats (*Cryptosporidium parvum*), or any combination thereof.

8. A biological indicator for monitoring sterility according to claim 7,
- wherein said optional surface layer is not present;
- wherein said substrate functional group is an amine, a hydroxyl, or a combination thereof;
- wherein said etiological agent is anthrax;
- wherein the amount of said silicon linking atoms is less than about 2%, and
- wherein said standard deviation is about 25% or less.

* * * * *